United States Patent [19]

Knowles

[11] Patent Number: 5,458,815
[45] Date of Patent: Oct. 17, 1995

[54] PHOTOCHROMIC NAPHTHOPYRAN COMPOUNDS

[75] Inventor: David B. Knowles, Apollo, Pa.

[73] Assignee: Transitions Optical, Inc., Pinellas Park, Fla.

[21] Appl. No.: 302,292

[22] Filed: Sep. 8, 1994

Related U.S. Application Data

[62] Division of Ser. No. 80,250, Jun. 21, 1993, Pat. No. 5,384,077.

[51] Int. Cl.$^6$ ............ G02B 5/23; G02B 27/00; C07D 405/10
[52] U.S. Cl. ............ 252/586; 524/94; 524/99; 546/167; 546/273; 548/454
[58] Field of Search ............ 549/389; 548/454; 546/273, 269, 167; 524/99, 94; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Chu | 252/586 |
| 4,816,584 | 3/1988 | Kwak et al. | 544/71 |
| 4,818,096 | 4/1988 | Heller et al. | 351/163 |
| 4,826,977 | 5/1989 | Heller et al. | 544/70 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,340,857 | 8/1994 | Van Gemert | 524/110 |
| 5,369,158 | 11/1994 | Knowles | 524/110 |

FOREIGN PATENT DOCUMENTS 816719  8/1937  France .

OTHER PUBLICATIONS

George A. Olah, *Friedel–Crafts and Related Reactions*, Interscience Publishers, vol. 3, Chap. XXXI, pp. 1–8, 82–88, 1964.

"Regioselective Friedel–Crafts Acylation of 1,2,3,4–Tetrahydroquinoline and Related Nitrogen Hetercycles", Ishihara, Yugi et al, J. Chem. Soc., Berkin Trans. 1, pp. 3401–3406, 1992.

R. C. Elderfield, *Heterocyclic Compounds*, 1951, vol. 2, Chapters 3 and 5, pp. 123–144, pp. 164–172.

*Organic Reactions*, vol. II, Chapter 1, "The Claisen Rearrangement" by D. Stanley Tarbell, pp. 26–27, R. Adams, Editor, John Wiley and Sons, Inc., 1944.

*Primary Examiner*—Nicky Chan
*Attorney, Agent, or Firm*—Frank P. Mallak; Irwin M. Stein

[57] ABSTRACT

Described are novel reversible photochromic naphthopyran compounds, examples of which are compounds substituted at the 3 position of the pyran ring with (i) an aryl substituent and (ii) a phenyl substituent having a 5- or 6-member heterocyclic ring fused at the number 3 and 4 carbon atoms of the phenyl substituent. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

18 Claims, No Drawings

PHOTOCHROMIC NAPHTHOPYRAN COMPOUNDS

This is a division of application Ser. No. 08/080,250, filed Jun. 21, 1993 now U.S. Pat. No. 5,384,077.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

The present invention relates to novel naphthopyran compounds whose colored forms have been found to have an unexpectedly higher absorption maxima than corresponding compounds having no substituents or different substituents at the same ring position. These compounds are substituted at the 3 position of the pyran ring with (i) an aryl substituent and (ii) a phenyl substituent having a 5- or 6-member heterocyclic ring fused at the number 3 and 4 carbon atoms of the phenyl substituent.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

Compounds, such as 3,3-diphenyl-3H-naphtho[2,1-b]pyran, change color on exposure to the near ultraviolet; but, at room temperature and above, this compound bleaches too rapidly for use in an ophthalmic lens. Substitution of either or both of the phenyl rings at the meta or para positions result in an even more rapid bleach rate, and therefore an even lower color intensity. The compound, 2,2-diphenyl-2H-naphtho[1,2-b]pyran, also colors on exposure to near ultraviolet light at room temperature but does not bleach in a reasonable period of time. Substitution of either or both of the phenyl rings at the meta or para positions have little effect on the rate of bleaching of these compounds.

In accordance with the present invention, it has now been discovered that certain novel naphthopyran compounds having a high quantum efficiency for coloring in the near ultraviolet and an acceptable rate of fade may be prepared. These compounds may be described as naphthopyrans substituted at the 3 position of the pyran ring with (i) an aryl substituent and (ii) a phenyl substituent having a 5- or 6-member heterocyclic ring fused at the number 3 and 4 carbon atoms of the phenyl substituent and may be represented by the following graphic formula:

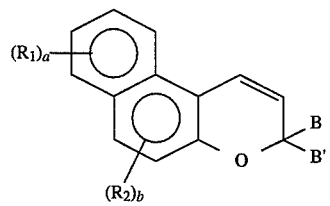

In graphic formula I, $R_1$ and $R_2$ may each be $C_1$-$C_{10}$ alkyl, $C_5$-$C_7$ cycloalkyl, e.g., cyclopentyl, cyclohexyl, and cycloheptyl, halogen, R(R')N-, or the group, —O—L, wherein R and R' are each hydrogen or $C_1$-$C_3$ alkyl, L is a $C_1$-$C_{12}$ alkyl, e.g., methyl, ethyl, propyl, butyl, pentyl, hexyl, heptyl, octyl, nonyl, decyl, undecyl, and dodecyl, phenyl($C_1$-$C_3$)alkyl, e.g., benzyl, phenethyl, phenylpropyl, mono-, di- and tri($C_1$-$C_3$) alkylphenyl, e.g., tolyl, xylyl, mesityl, and cumenyl, $C_1$-$C_5$ alkylcarbonyl, and halo($C_1$-$C_4$)alkylcarbonyl, which includes mono-, di-, or tri-halo substituents, $C_1$-$C_4$ monoalkylaminocarbonyl, acetonyl, pyridyl, substituted or unsubstituted arylcarbonyl, said aryl group being phenyl or naphthyl, said aryl substituents being $C_1$-$C_4$ alkyl, $C_1$-$C_4$ alkoxy, e.g., methoxy, ethoxy, propoxy, and butoxy, halogen, $C_5$-$C_7$ cycloalkyl, or $C_1$-$C_4$ alkyl substituted $C_5$-$C_7$ cycloalkyl, said halogen (or halo) groups described above being chloro, fluoro, or bromo, and a and b are each the integers 0, 1 or 2 provided that the sum of a and b is not more than 2.

Preferably, $R_1$ and $R_2$ are each R(R')N-, or the group, —O—L, wherein R and R' are each hydrogen or $C_1$-$C_2$ alkyl, L is $C_1$-$C_4$ alkyl, $C_1$-$C_2$ alkylphenyl, phenyl($C_1$-$C_2$)alkyl, $C_1$-$C_2$ alkylcarbonyl, halo($C_1$-$C_2$)alkylcarbonyl, or $C_1$-$C_2$ monoalkylaminocarbonyl, said halo group being chloro or fluoro, and a and b are each the integer 0 or 1.

B may be the substituted or unsubstituted aryl group, naphthyl or phenyl, said aryl substituents being $C_1$-$C_5$ alkyl, halo($C_1$-$C_5$)alkyl, hydroxy, $C_1$-$C_5$ alkoxy, $C_1$-$C_4$ alkoxy($C_1$-$C_4$)alkyl, halogen, or R(R')N-, wherein R and R' are each hydrogen or $C_1$-$C_3$ alkyl, said halogen (or halo) groups being fluorine, chlorine, or bromine. Preferably, B is represented by the following graphic formula II:

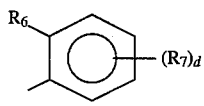

In graphic formula II, $R_6$ is hydrogen, $C_1$-$C_4$ alkyl, $C_1$-$C_4$ alkoxy, fluoro, or chloro and each $R_7$ is a $C_1$-$C_4$ alkyl, $C_1$-$C_4$ alkoxy, hydroxy, chloro, or fluoro and d is an integer from 0 to 2.

B' may be represented by one of the following graphic formulae III or IV:

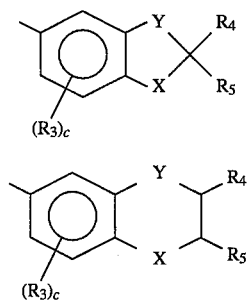

In graphic formula III and IV, X is oxygen or nitrogen and Y is carbon or oxygen, provided that when X is nitrogen, Y is carbon; $R_4$ and $R_5$ are each hydrogen or $C_1$-$C_5$ alkyl; each $R_3$ is a $C1$-$C_5$ alkyl, $C_1$-$C_5$ alkoxy, hydroxy, or halogen, said halogen substituent being chloro, fluoro, or bromo, and c is an integer from 0 to 3, e.g., 0, 1, 2, or 3. Preferably, B' is represented by graphic formula III, wherein X is oxygen; Y is carbon or oxygen; $R_4$ and $R_5$ are each hydrogen or $C_1$-$C_4$ alkyl; each $R_3$ is a $C_1$-$C_4$ alkyl, $C_1$-$C_4$ alkoxy, hydroxy, or fluoro; and c is the integer 0, 1, or 2.

In graphic formula III, when X is oxygen and Y is carbon and c is zero, the group is a 2,3-dihydrobenzofuran-5-yl; when X is oxygen and Y is oxygen and c is zero, the group is 1,3-benzo-dioxole- 5-yl; and when X is nitrogen and Y is carbon and c is zero, the group is indoline-5-yl. In graphic formula IV, when X is oxygen and Y is carbon, the unsubstituted group is a chroman-6-yl; when X is oxygen and Y is oxygen, the unsubstituted group is a 1,4-benzodioxan-6-yl; and when X is nitrogen and Y is carbon, the unsubstituted group is 1,2,3,4-tetrahydroquinoline-6-yl. For brevity, these groups will be referred to herein as fused heterocyclic-phenyl groups.

Compounds represented by graphic formula I are prepared by Friedel-Crafts methods using an appropriately substituted or unsubstituted benzoyl chloride of graphic formula V with a commercially available fused heterocyclic-benzene compound to produce B' structures of graphic formula III or IV. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992. If a fused heterocyclic-benzene compound containing an oxygen is not commercially available, it may be prepared from an appropriately substituted phenol as described in *Organic Reactions*, Vol. II, pages 26 and 27.

In reaction A shown below, the compounds represented by graphic formulae V and III are dissolved in a solvent, such as carbon disulfide or methylene chloride, in the presence of a Lewis acid, such as aluminum chloride, to form the corresponding heterocyclic fused benzophenone represented by graphic formula VII.

REACTION A

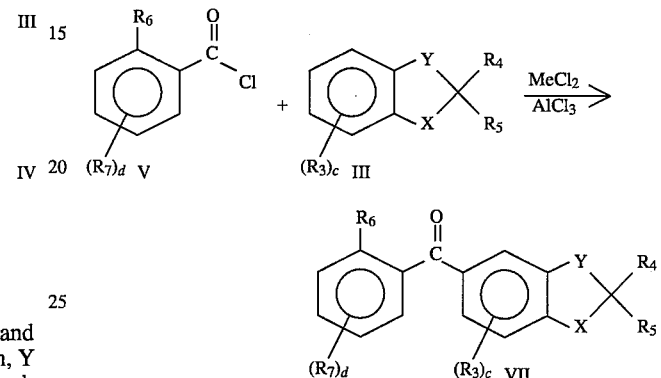

In reaction B shown below, the heterocyclic fused benzophenone represented by graphic formula VII is reacted with sodium acetylide in a suitable solvent, such as dry tetrahydrofuran, to form the corresponding propargyl alcohol represented by graphic formula VIII.

REACTION B

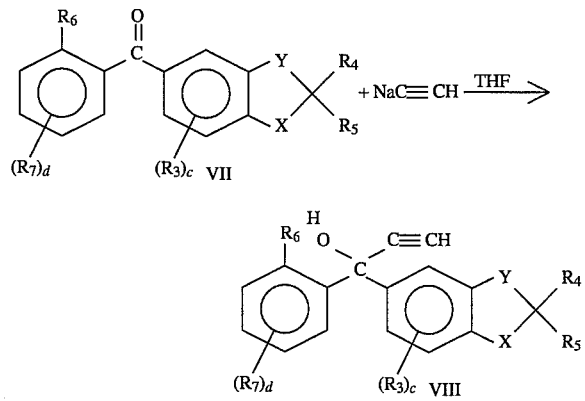

In reaction C shown below, the propargyl alcohol represented by graphic formula VIII is coupled with the appropriately substituted 2-naphthol, represented by graphic formula IX, under acidic conditions to form the naphthopyrans of graphic formula X, which are compounds represented by graphic formula I.

REACTION C

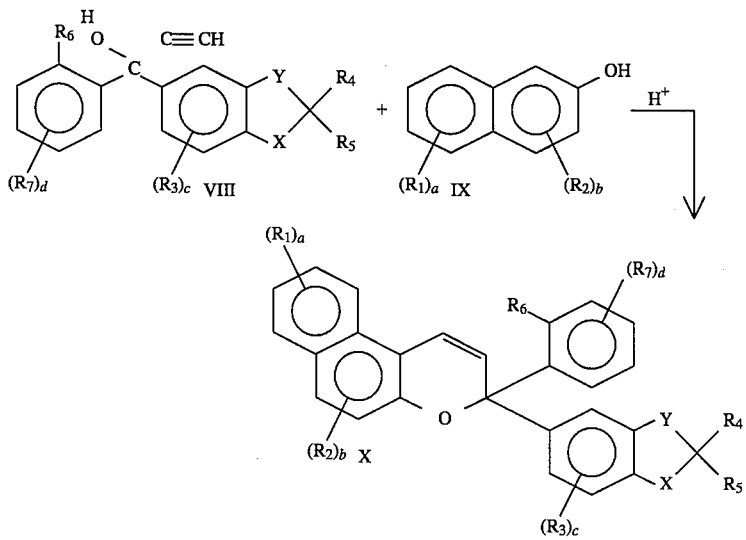

By substituting the fused heterocyclic-phenyl group of graphic formula IV for that of graphic formula III in reaction A, compounds similar to those represented by graphic formula X except for a 6-member heterocyclic ring fused at the number 3 and 4 carbon atoms of the 3-phenyl substituent may be prepared.

Compounds represented by graphic formula I may be used in those applications in which organic photochromic substances may be employed, such as optical lenses, e.g., ophthalmic and plano lenses, face shields, goggles, visors, camera lenses, windows, automotive windshields, aircraft and automotive transparencies, e.g., T-roofs, sidelights, and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to orange.

Examples of contemplated naphthopyrans within the scope of the invention are the following:

(1) 3-(2,3-dihydrobenzofuran-5-yl)-3-phenyl-3H-naphtho-[ 2,1-b]pyran;

(2) 3-(2,3-dihydrobenzofuran-5-yl)-3-(2-fluorophenyl)-3H-naphtho[2,1-b]pyran;

(3) 3-(2,3-dihydrobenzofuran-5-yl)-3-(2-methoxyphenyl)-3H-naptho[2,1-b]pyran;

(4) 5-acetoxy-3-(2,3-dihydrobenzofuran-5-yl)-3-(2-fluorophenyl)- 3H-naphtho[2,1-b]pyran;

(5) 8-methoxy-3-(2,3-dihydrobenzofuran-5-yl)-3-(2-fluorophenyl)- 3H-naphtho[2,1-b]pyran;

(6) 3-(4-methoxyphenyl)-3-(2,4,7-trimethyl-2,3-dihydrobenzofuran- 5-yl)-3H-naphtho[2,1-b]pyran;

(7) 3-(2-methyldihydrobenzofuran-5-yl)-3-(2-fluorophenyl)- 3H-naphtho[2,1-b]pyran;

(8) 3-(1,4-benzodioxan-6-yl)-3-(2-fluorophenyl)-3H-naphtho[ 2,1-b]pyran;

(9) 3-(1,3-benzodioxole-5-yl)-3-phenyl-3H-naphtho-[ 2,1-b]pyran;

(10) 3-(indoline-5-yl)-3-phenyl-3H-naphtho[2,1-b]pyran; and

(11) 3-(1,2,3,4-tetrahydroquinoline-6-yl)-3-phenyl-3H-naphtho[ 2,1-b]pyran.

Commercially available photoreactive inorganic glass lenses containing silver halide particles darken to a neutral gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired gray or brown color shade when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound.

Particularly contemplated classes of complementary organic photochromic compounds that may be used include: the purple/blue spiro(indoline) benzoxazines described in U.S. Pat. No. 4,816,584; spiro(indoline) pyridobenzoxazine photochromic compounds described in U.S. Pat. No. 4,637, 698; spiro(indoline) naphthoxazines described in U.S. Pat. Nos. 3,562,172, 3,578,602, 4,215,010 and 4,342,668; and benzopyrans and naphthopyrans having a nitrogen-containing substituent in the 2-position of the pyran ring, as described in U.S. Pat. No. 4,818,096. All of the aforedescribed oxazine- and pyran-type organic photochromic compounds are reported to exhibit a color change of from colorless to purple/blue on exposure to ultraviolet light. The disclosures of said U.S. Patents are incorporated herein by reference.

Other contemplated complementary organic photochromic compounds that are reported to exhibit a color change of from colorless to yellow/orange when exposed to UV light that may be used in combination to augment the yellow/orange color of the naphthopyran compounds of the present invention include: benzopyrans and naphthopyrans having a spiro adamantane group in the 2-position of the pyran ring, as described in U.S. Pat. No. 4,826,977; and naphthopyran compounds described in U.S. Pat. No. 5,066, 818.

The naphthopyran compounds of the present invention may be used in admixture with or in conjunction with the aforedescribed complementary or augmenting organic photochromic compounds in amounts and in a ratio such that an organic host material to which the mixture of compounds is applied or in which they are incorporated exhibits a substantially neutral color when activated with unfiltered sunlight, i.e., as near a neutral gray or brown color as possible given the colors of the activated photochromic compounds. The relative amounts of the photochromic compounds used will vary and depend in part upon the relative intensities of the color of the activated species of such compounds.

For example, the naphthopyran compounds of the present invention may be combined with one or more of the aforedescribed purple/blue oxazine- and/or pyran-type organic photochromic compounds in amounts and in a ratio such that an organic host material to which the mixture of compounds is applied or in which they are incorporated exhibits a near-brown color. Generally, the weight ratio of the aforedescribed oxazine- and pyran-type compound(s) to the naphthopyran compound(s) of the present invention will vary from about 1:3 to about 3:1, e.g., between about 1:2 or 0.75:1 and about 2:1.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/X+Y+Z$ and $y=Y/X+Y+Z$. Color as described in the CIE system can be plotted on a chromaticity diagram, usually a plot of the chromaticity coordinates x and y. See pages 47–52 of *Principles of Color Technology*, by F. W. Billmeyer, Jr. and Max Saltzman, Second Edition, 3John Wiley and Sons, N.Y. (1981).

The amount of photochromic substance or composition-containing same applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity.

Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. See U.S. Pat. No. 5,066,818 column 14, line 41 to column 15, line 25 for examples of the above methods.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Examples of host materials which may be used with the photochromic substances or compositions described herein include: polymers, i.e., homopolymers and copolymers, of polyol(allyl carbonate) monomers, e.g., diethylene glycol bis(allyl carbonate), polymers, i.e., homopolymers and copolymers, of polyfunctional acrylate monomers, polyacrylates, which are polymers of esters of acrylic acid or methacrylic acid, such as methyl acrylate and methyl methacrylate, cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, i.e., poly(4,4'-dioxydiphenol- 2,2-propane), which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark, CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653, cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substance is in an inactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The present invention is more particularly described in the following examples which are intended as illustrative only, since numerous modifications and variations therein will be apparent to those skilled in the art.

EXAMPLE 1

Step 1

2,3-dihydrobenzofuran (9.25 grams, 0.077 moles) was added to a reaction flask containing 100 milliliters of methylene chloride and 10.8 grams (0.077 moles) of benzoyl chloride. Aluminum chloride (12.32 grams, 0.092 moles) was added slowly and the resulting mixture was stirred for 2 hours under a nitrogen atmosphere. The reaction mixture was added to a 5 percent aqueous hydrochloric acid solution and stirred until colorless. The organic layer was separated and the aqueous layer was back extracted with 100 milliliters of methylene chloride. The organic portions were combined and added to a 10 percent aqueous sodium hydroxide solution containing 1 milliliter of triethylamine to remove any unreacted starting material. The mixture was stirred and the organic layer was separated and dried over magnesium sulfate. The residual methylene chloride was removed under vacuum. The resulting pale yellow oil was induced to crystallize by dissolving it in hexane and then cooling the solution in a dry ice/acetone bath. 7.8 grams of the crystalline product, 5-benzoyl-2,3-dihydrobenzofuran, was collected by vacuum filtration.

Step 2

5-benzoyl-2,3-dihydrobenzofuran (7.8 grams, 0.035 mole) from Step 1 was added to a reaction flask containing 300 milliliters of tetrahydrofuran saturated with acetylene. 10.0 grams of a 18 weight percent suspension of sodium acetylide in xylene/mineral oil (0.035 moles of sodium acetylide) was added slowly to the stirred solution. After 16 hours at room temperature and under a nitrogen atmosphere, the reaction mixture was dissolved in 5 percent aqueous hydrochloric acid solution. The resulting mixture was extracted with three 100 milliliter portions of methylene chloride. The organic extracts were combined and dried over magnesium sulfate. The solvent, methylene chloride, was removed under vacuum to yield 7.0 grams of the product containing 1-(2,3-dihydrobenzofuran-5-yl)- 1-phenyl-2-propyn-1-ol which was not purified further but used directly in the next step.

Step 3

The product (7.0 grams) from Step 2 was added to a reaction flask containing 300 milliliters of benzene and 4.0 grams of 2-hydroxynaphthalene. A catalytic amount of dodecylbenzenesulfonic acid (3 drops) was added. The mixture was heated to 40° C. and stirred for 1 hour under a nitrogen atmosphere. Afterwards, the reaction mixture was dissolved in distilled water and washed with about 300 milliliters of 10 percent aqueous sodium hydroxide. The organic layer was separated, dried over magnesium sulfate and the remaining benzene was removed under vacuum. The resulting residue was induced to crystallize by dissolving it in a hexane/ether mixture and cooling the mixture in a dry ice/acetone bath. The resulting crystals were collected by vacuum filtration, dissolved in a 9:1 mixture of hexane:ethyl acetate, stirred for one half hour, and collected by vacuum filtration. The crystalline product, about 3.0 grams, melted at 128°–131° C. and was 97.7% pure as determined by liquid chromatographic analysis. A nuclear magnetic resonance (NMR) spectrum showed the solid crystalline product to have a structure consistent with 3-(2,3-dihydrobenzofuran-5-yl )-3-phenyl-3H-naphtho-[ 2,1-b ] pyran.

EXAMPLE 2

The procedure of Step 1 of Example 1 was utilized except for the following: 2-fluorobenzoyl chloride (13.2 grams, 0.083 mole) was used instead of benzoyl chloride; the mixture was stirred for one hour; and the combined organic fraction was back extracted with distilled water. 19.5 grams of product containing 5-(2-fluorobenzoyl- 2,3-dihydrobenzofuran was recovered.

The procedure of Step 2 of Example 1 was utilized except that 5-(2-fluorobenzoyl)-2,3-dihydrobenzofuran (8 grams, 0.033 moles) was used as the reactant; the reaction mixture was stirred 20 hours; 10% aqueous hydrochloric acid was used to dissolve the reaction mixture; and the combined organic fraction was washed with two portions of water, about 300 milliliters each. The yield of product containing 1-(2,3-dihydrobenzofuran-5-yl)-1-(2-fluorophenyl)- 2-propyn-1-ol was 7.0 grams.

The procedure of Step 3 of Example 1 was utilized except that 1-(2,3-dihydrobenzofuran-5-yl)-1-(2-fluorophenyl)-2-propyn-1-ol (7.0 grams), toluene (300 milliliters), and a catalytic amount of p-toluenesulfonic acid (3 drops) were used; and the reaction mixture was heated to 45° C. After the organic layer was separated, the aqueous layer was washed once with about 100 milliliters of methylene chloride and the organic fractions were combined. The combined organic extracts were dried over magnesium sulfate and reduced under vacuum to yield 7.0 grams of oil.

The oil was purified using a silica gel column and a 1:4 mixture of ethyl acetate:hexane as the eluant. The photochromic fractions were collected, combined and the remaining eluant was removed under vacuum. The crystals were isolated as described in Step 3 of Example 1. The crystalline product, 3.0 grams, melted at 110°–113° C. and was 99.8% pure as determined by liquid chromatographic analysis. A nuclear magnetic resonance (NMR) spectrum showed the solid crystalline product to have a structure consistent with 3-(2,3-dihydrobenzofuran-5-yl)-3-(2-fluorophenyl)-3H-naphtho[2,1-b]-pyran.

EXAMPLE 3

The procedure of Step 1 of Example 1 was followed except that 2-anisoyl chloride (14.2 grams, 0.083 moles) was used as the reactant instead of benzoyl chloride and the reaction mixture was stirred for one hour. 16.7 grams of the crystalline product, 5-(2-methoxybenzoyl)-2,3-dihydrobenzofuran, was recovered and used in the next step. The procedure of Step 2 of Example 1 was followed except that the combined organic fraction was washed with distilled water. The yield of product containing 1-(2,3-dihydrobenzofuran- 5-yl)-1-(2-methoxyphenyl)-2-propyn-1-ol was 16.7 grams.

The procedure of Step 3 of Example 1 was utilized except that the product containing 1-(2,3-dihydrobenzofuran-5-yl)-1-(2-methoxyphenyl)-2-propyn-1-ol and a catalytic amount of p-toluenesulfonic acid were used; the reaction mixture was heated to 35° C.; and the oil purification procedure of Example 2 was used. The resulting crystalline product, 3.7 grams, melted at 142°–144° C. and was 99.5% pure as determined by liquid chromatographic analysis. A nuclear magnetic resonance (NMR) spectrum showed the solid crystalline product to have a structure consistent with 3-(2,3-dihydrobenzofuran-5-yl)-3-(2-methoxyphenyl)-3H-naphtho-[2,1-b]pyran.

EXAMPLE 4

The procedure of Step 1 of Example 1 was utilized except that 2-fluorobenzoyl chloride (13.2 grams, 0.083 mole) was used as the reactant instead of benzoyl chloride, the mixture was stirred for one hour, and the combined organic fraction was back extracted with distilled water. 19.5 grams of product containing 5-(2-fluorobenzoyl)-2,3-dihydrobenzofuran was recovered. The procedure of Step 2 of Example 1 was followed except that 5-(2-fluorobenzoyl)-2,3-dihydrobenzofuran (5 grams, 0.02 mole) was used and the combined organic fraction was washed with distilled water. The yield of product, a yellow oil containing 1-(2,3-dihydrobenzofuran-5-yl)-1-(2-fluorophenyl)-2-propyn-1-ol, was 4.3 grams.

The procedure of Step 3 of Example 1 was utilized except that 1-(2,3-dihydrobenzofuran-5-yl)-1-(2-fluorophenyl)-2-propyn-1-ol (4.3 grams) from Step 2, 3-acetoxy-2-naphthol (3.3 grams, 0.016 mole), and a catalytic amount of p-toluenesulfonic acid were used; the reaction mixture was heated to 45° C.; and the oil purification procedure of Example 2 was used. The resulting crystalline product, 4.6 grams, melted at 156°–157° C. and was 99.0% pure as determined by liquid chromatography analysis. A nuclear magnetic resonance (NMR) spectrum showed the solid crystalline product to have a structure consistent with 5-acetoxy-3-(2,3-dihydrobenzofuran-5-yl)-3-(2-fluorophenyl)- 3H-naphtho[2,1-b]-pyran.

EXAMPLE 5

The procedure of Step 1 of Example 1 was followed except that 2-fluorobenzoyl chloride (13.2 grams, 0.083 mole) was used as the reactant instead of benzoyl chloride and the mixture was stirred for one hour. 16.0 grams of the product, 5-(2-fluorobenzoyl)-2, 3-dihydrobenzofuran, was recovered. The procedure of Step 2 of Example 1 was followed using 5-(2-fluorobenzoyl)-2,3-dihydrobenzofuran (12.5 grams, 0.051 mole) from Step 1. The yield of product, containing 1-(2,3-dihydrobenzofuran-5-yl)-1-(2-fluorophenyl)- 2-propyn-1-ol, was 11.0 grams.

The procedure of Step 3 of Example 1 was utilized except that 1-(2,3-dihydrobenzofuran-5-yl)-1-(2-fluorophenyl)-2-propyn-1-ol (5.0 grams) from Step 2, 6-methoxy-2-hydroxynaphthalene, and a catalytic amount of p-toluenesulfonic acid were used; the reaction mixture was heated to 35° C. and stirred for 1.5 hours; and the oil purification procedure of Example 2 was used. The resulting crystalline product, 4.3 grams, melted at 164°–167° C. and was 95.0% pure as determined by liquid chromatographic analysis. A nuclear magnetic resonance (NMR) spectrum showed the solid crystalline product to have a structure consistent with 8-methoxy-3-(2,3-dihydrobenzofuran- 5-yl)-3-(2-fluorophenyl)-3H-naphtho[2,1-b] pyran.

EXAMPLE 6

Step 1

2,5-dimethylphenol (30.0 grams, 0.25 mole) was added to a reaction flask containing 300 milliliters of ethyl alcohol and 17.0 grams (0.3 mole) of potassium hydroxide. Allyl bromide (36.3 grams, 0.3 mole) was added slowly to the stirred solution over a period of 15 minutes. The reaction mixture was refluxed in a nitrogen atmosphere for four hours. The excess solvent was removed under vacuum and the residual solid was dissolved in 200 milliliters of 5% aqueous sodium hydroxide and extracted with three portions of methylene chloride, about 100 milliliters each. The organic extracts were combined, dried over magnesium sulfate, and reduced under vacuum to yield 33.3 grams of a yellow oil containing the desired product, 2,5-dimethylphenyl allyl ether.

Step 2

2,5-dimethylphenyl allyl ether (33.3 grams, 0.21 mole) from Step 1 was added to a reaction flask equipped with a water condenser and heated to 195° C with stirring under a nitrogen atmosphere. After 2 hours, the temperature was reduced to 140° C. and several drops of dodecylbenzenesulfonic acid were added. The reaction mixture was slowly heated to 195° C. and held there for 3 hours. The reaction mixture was cooled and dissolved in 5% aqueous sodium hydroxide. The resulting mixture was extracted with three 100 milliliter portions of methylene chloride. The organic extracts were combined, dried over magnesium sulfate and reduced under vacuum. The resulting product was distilled at a head temperature of 80° C. under a reduced pressure of 6 mm Hg to yield 11.0 grams of a clear colorless oil. A nuclear magnetic spectrum (NMR) showed the product to have a structure consistent with 2,3-dihydro-2,4,7-trimethylbenzofuran.

Step 3

2,3-dihydro-2,4,7-trimethylbenzofuran (5.0 grams, 0.031 mole) from Step 2 was added to a reaction flask containing 300 milliliters of methylene chloride and 5.3 grams (0.031 mole) of p-anisoyl chloride. Aluminum chloride (5.0 grams, 0,037 mole) was added slowly to the stirred solution. After 1.5 hours the reaction mixture was dissolved in 20% aqueous hydrochloric acid and stirred for 10 minutes. The organic layer was separated and the aqueous layer was washed once with 100 milliliters of methylene chloride. The organic extracts were combined, washed with about 200 milliliters of distilled water, separated, and dried over magnesium sulfate. The solvent, methylene chloride, was removed under vacuum to yield 7.0 grams of product containing the desired ketone, 5-(4-methoxybenzoyl)-2,4,7-trimethyl-dihydrobenzofuran.

Step 4

5-(4-methoxybenzoyl)-2,4,7-trimethyldihydrobenzofuran (7.0 grams, 0.024 mole) from Step 3 was added to a reaction flask containing 300 milliliters of tetrahydrofuran saturated with acetylene. 8.1 grams of a 18 weight percent solution of sodium acetylide in xylene/light mineral oil (0.028 mole of sodium acetylide) was added to the stirred solution. After 72 hours the reaction mixture was dissolved in 10% aqueous hydrochloric acid and extracted with three portions of methylene chloride, about 100 milliliters each. The organic extracts were combined and dried over magnesium sulfate. The methylene chloride was removed under vacuum. The product containing 1-(2,3-dihydro-2,4,7-trimethylbenzofuran)- 5-yl-1-(4-methoxyphenyl)-2-propyn-1-ol was used directly in the next step.

Step 5

1-(2,3-dihydro-2,4,7-trimethylbenzofuran)-5-yl-1-(4-methoxyphenyl)- 2-propyn-1-ol (5.0 grams) from Step 4 was added to a reaction flask containing 300 milliliters of benzene and 2.3 grams (0.016 mole) of 2-hydroxynaphthalene. A catalytic amount of p-toluenesulfonic acid was added to the stirred solution and the mixture was heated to 35° C. under a nitrogen atmosphere. After 1.5 hours, the reaction mixture was dissolved in 20% aqueous sodium hydroxide and extracted with three portions of methylene chloride, about 100 milliliters each. The organic extracts were combined and dried over magnesium sulfate. The methylene chloride was removed under vacuum. The product was purified using a silica gel column and a 1:4 mixture of ethyl acetate:hexane as the eluant. The photochromic fractions were combined and the remaining eluant was removed under vacuum. The residual oil was crystallized from hexane to yield 200 mg. of the desired photochromic compound. The crystalline product melted at 162°–164° C. and was 98.8% pure as determined by liquid chromatographic analysis. A nuclear magnetic resonance (NMR) spectrum showed the solid crystalline product to have a structure consistent with 3-(4-methoxyphenyl)-3-(2,4,7-trimethyldihydrobenzofuran-5-yl)-3H-naphtho[2,1-b]pyran.

EXAMPLE 7

2-methyldihydrobenzofuran was prepared by the method described in Example 6, Steps 1 and 2, using phenol instead of 2,5-dimethyl phenol in Step 1. For further information respecting the synthesis, see *Organic Reactions*, Volume II, pages 26 and 27. The procedures of Steps 1, 2, and 3 of Example 1 were followed using 2-methyldihydrobenzofuran in place of 2,3-dihydrobenzofuran in Step 1. The resulting product was 98.6% pure as determined by liquid chromatographic analysis. A nuclear magnetic resonance (NMR) spectrum showed the product to have a structure consistent with 3-(2-methyldihydrobenzofuran-5-yl)-3-(2-fluorophenyl)-3H-naphtho-[ 2,1-b]pyran.

EXAMPLE 8

The procedure of Step 1 of Example 1 was utilized except that 2-fluorobenzoyl chloride (5.0 grams, 0.032 mole) was used instead of benzoyl chloride; 1,4-benzodioxan (4.4 grams, 0,032 mole) was used instead of 2,3-dihydrobenzofuran; and the reaction mixture was stirred for 1 hour. 8.0 grams of the white crystalline product, 5-(2-fluorobenzoyl)-1,4-benzodioxan, was recovered. The procedure of Step 2 of Example 1 was followed except that 5-(2-fluorobenzoyl)-1,4-benzodioxan (8.0 grams, 0.031 mole) was used and the reaction mixture was stirred for 20 hours. The yield of product containing 1-(1,4-benzodioxan-6-yl)-1-(2-fluorobenzoyl)-2-propyn- 1-ol was 7.0 grams.

The procedure of Step 3 of Example 1 was utilized except that product containing 1-(1,4-benzodioxan-6-yl)-1-(2-fluorobenzoyl)- 2-propyn-1-ol (7.0 grams) from Step 2, 2-naphthol (3.6 grams), and a catalytic amount of p-toluenesulfonic acid were used; the mixture was stirred for 2 hours; and the oil purification procedure of Example 2 was used. The resulting crystalline product, about 0.5 gram, melted at 143°–147° C. and was 97.3% pure as determined by liquid chromatographic analysis. A nuclear magnetic resonance (NMR) spectrum showed the solid crystalline product to have a structure consistent with 3-(1,4-benzodioxan-6-yl)-3-(2-fluorophenyl)- 3H-naphtho[2,1-b]pyran.

EXAMPLE 9

Step 1

Piperonal (10.0 grams, 0.067 moles) was added to a reaction flask containing 100 milliliters of tetrahydrofuran. Phenyl magnesium bromide (0.08 moles) was added slowly and the resulting mixture was heated to 66° C. and stirred for 1 hour under a nitrogen atmosphere. The reaction mixture was added to a 5 percent aqueous hydrochloric acid and ice solution. The organic layer was separated and the aqueous layer was washed with three 100 milliliter portions of methylene chloride. The organic portions were combined and dried over magnesium sulfate. The residual methylene chloride was removed under vacuum. About 15.0 grams of a white/yellow oil product was recovered. A nuclear magnetic resonance (NMR) spectrum showed the product to be consistent with alpha-phenyl-1,3-benzodioxole-5-methanol.

Step 2

Alpha-phenyl-1,3-benzodioxole-5-methanol (10.0 grams, 0.044 mole) from Step 1 was dissolved in a reaction flask containing 300 milliliters of methylene chloride and pyridinium dichromate (25.0 grams, 0.066 mole) was added. After 16 hours at room temperature and under a nitrogen atmosphere, the reaction mixture was diluted with diethyl ether and vacuum filtered to remove the solids. The liquid portion was subjected to evaporation to yield 8.3 grams of a slightly viscous off white oil. A nuclear magnetic resonance (NMR) spectrum showed the product to have a structure consistent with 5-benzoyl-1,3-benzodioxole.

Step 3

The procedure of Step 2 of Example 1 was followed except that 5-benzoyl-1,3-benzodioxole (8.3 grams) was used as a reactant instead of 5-(benzoyl)-2,3-dihydrobenzofuran and after the reaction mixture was stirred for 22 hours at room temperature, the pH was reduced to about 2.0. The yield of product containing Step 4 1-(1,3-benzodioxole-5-yl)-1-phenyl-2-propyn-1-ol was 9.0 grams.

1-(1,3-benzodioxole-5-yl)-1-phenyl-2-propyn-1-ol (3.5 grams, 0.014 mole) from Step 3 and 2-naphthol (2.0 grams, 0.014 mole) were added to a reaction flask containing 300 milliliters of toluene. A catalytic amount of p-toluenesulfonic acid was slowly added and the reaction mixture was stirred for 2 hours at room temperature under a nitrogen atmosphere. Afterwards, the reaction mixture was added to 200 milliliters of 20% aqueous sodium hydroxide and washed. The organic layer was separated and dried over magnesium sulfate. The solids were filtered and the resulting oil was purified on a silica gel column using chloroform as the eluant. The resulting orange oil was induced to crystallize by dissolving it in a hexane/ether mixture and cooling the mixture in a dry ice/acetone bath. The resulting crystals were collected by vacuum filtration. The crystalline product, about 4.1 grams, melted at 168°–170° C. and was 99.8% pure as determined by liquid chromatographic analysis. A nuclear magnetic resonance (NMR) spectrum showed the solid crystalline product to have a structure consistent with 3-(1,3-benzodioxole-5-yl)-3-phenyl-3H-naphtho[2,1-b]pyran.

COMPARATIVE EXAMPLE 1

1,1-diphenyl-2-propyn-1-ol (20.8 grams, 0.1 mole) was added to a reaction flask containing 200 milliliters of benzene and 15 grams of 2-naphthol. The reaction mixture was warmed to 55° C. and after all of the 2-naphthol was dissolved, 0.25 grams of p-toluenesulfonic acid was added to the stirred reaction mixture. The mixture changed from light tan to dark black, became exothermic, and the temperature rose to 70° C. After a few minutes, the reaction mixture lightened and began to cool. After 30 minutes, the reaction mixture was poured into 100 milliliters of 10 percent aqueous sodium hydroxide and shaken. The organic phase was washed once with 10 percent aqueous sodium hydroxide and then washed with water. The solvent, benzene, was removed on a rotary evaporator. The resulting light tan solid residue was slurried with 100 milliliters of hexane and filtered. The filtered solid was washed again with 100 milliliters of hexane and dried to provide 18.4 grams of the product, 3,3-diphenyl-3H-naphtho[2,1-b]pyran. The solid product had a melting point of 156°–158° C. and was 98 percent pure as determined by liquid chromatographic analysis.

COMPARATIVE EXAMPLE 2

Anisole (10.8 grams, 0.1 mole) and benzoyl chloride (14 grams, 0.1 mole) were dissolved in 200 milliliters of hexane and stirred at room temperature. Anhydrous aluminum chloride, 15 grams, was added slowly to the reaction mixture over a period of 15 minutes. The reaction mixture was stirred an additional 15 minutes. The hexane was decanted and the resulting viscous residue was carefully hydrolyzed with 200 milliliters of a mixture of ice and dilute hydrochloric acid. The organic fraction was taken up in dichloromethane and the resulting solution was washed with water. Dichloromethane was removed on a rotary evaporator leaving an oil product that solidified on standing. The solidified product was broken-up, washed with two 50 milliliter portions of pentane, and dried, yielding 4-methoxybenzophenone.

10 grams of this 4-methoxybenzophenone was converted to the propargyl alcohol by the procedure described in Step 2 of Example 1. NMR analysis of the resulting product showed it to be a mixture of compounds having structures consistent with 1-phenyl-1(4-methoxyphenyl)-2-propyn-1-ol and the starting ketone, 4-methoxybenzophenone, in a ratio of 3:1.

The crude propargyl alcohol was added to a reaction flask containing a slurry of 5 grams of 2-naphthol, 40 grams of anhydrous acid alumina and 200 milliliters of toluene. The resulting reaction mixture was heated to reflux for 30 minutes, cooled, and filtered. The alumina was washed two times with 100 milliliter portions of hexane. The toluene and hexane fractions were combined and the organic solvents were removed on a rotary evaporator. The resulting product was an orange oil that was induced to crystallize by dissolving it in a mixture of hexane and diethyl ether and then cooling the solution in a dry ice/acetone bath. The product crystals were washed with diethyl ether and dried to yield 1.4 grams of a product having a melting point of 149°–150° C. A nuclear magnetic resonance (NMR) spectrum showed the solid product to have a structure consistent with 3-phenyl-3(4-methoxyphenyl )-3H-naphtho [2,1-b]pyran.

COMPARATIVE EXAMPLE 3

The procedures of Steps 1 and 2 of Example 1 were followed except that anisole was used instead of 2,3-dihydrobenzofuran and 2-fluorobenzoyl chloride was used instead of benzoyl chloride in Step 1. The resulting product contained 1-(4-methoxy-3-methylphenyl)- 1-(2-fluorophenyl)-2-propyn-1-ol. The procedure of Step 3 of Example 1 was utilized except that 1-(4-methoxy-3-methylphenyl)-1-(2-fluorophenyl)-2-propyn-1-ol (5.5 grams, 0.02 mole) from the previous step, 2-naphthol (3.0 grams), and a catalytic amount of p-toluenesulfonic acid were used; and the reaction mixture was heated to 35° C. and stirred for several hours.

The resulting oil product was purified on a silica gel column using a 1:5 mixture of ethyl acetate:hexane as the first eluant followed by a 1:1 mixture of chloroform:hexane as the second eluant. The filtrate was collected and the solvent was removed to yield 2.0 grams of a solid product. The solid product had a melting point of 98° C. and was 99% pure as determined by liquid chromatographic analysis. A nuclear magnetic resonance (NMR) spectrum showed the solid product to have a structure consistent with 3-(4-methoxy-3-methylphenyl)-3-(2-fluorophenyl)-3H-naphtho-[2,1-b]pyran.

EXAMPLE 10

Part A

The naphthopyran prepared in Example 9 was incorporated into an ethyl cellulose resin by the following procedure. 25 milligrams of the photochromic compound was added to 2.0 grams of a 10 weight percent ethyl cellulose solution in toluene. The naphthopyran compound was dissolved by warming and stirring on a steam bath. Approximately 2.0 grams of the resultant solution was deposited on the edge of a 75 by 25 millimeter (mm) glass slide. Using a draw down bar, an 8 mm layer of photochromic resin solution was placed evenly on the slide and permitted to dry.

Part B

Further testing was done on selected naphthopyrans that were imbibed by thermal transfer into test squares of a homopolymer of diethylene glycol bis(allyl carbonate) by the following procedure. Each naphthopyran was dissolved into toluene solvent to form a 4 weight percent solution of the compound. A piece of No. 4 Whatman filter paper was saturated with the naphthopyran solution and allowed to air dry. The dried filter paper was placed on one side of the polymer test square, which measured ⅛ inch (0.3 centimeter)×2 inch (5.1 centimeters)×2 inch (5.1 centimeters). A piece of untreated filter paper was placed on the other side of the polymer test square and the resulting sandwich placed between two plates of flat aluminum metal plates. The entire assembly was then placed in a 155° C. oven for a time sufficient to thermally transfer the naphthopyran into the polymer test square. Residence times in the oven were adjusted to imbibe comparable amounts of the naphthopyran compounds in order to yield a comparable UV absorbance at 347 nm. The imbibed test squares were washed with acetone after removal from the oven.

Part C

Both sets of polymer test samples were tested for photochromic response rates on an optical bench. The samples were illuminated by a 150 watt Xenon lamp fitted with a copper sulfate bath and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The $\Delta$ OD/Min, which represents the sensitivity of the photochromic compound's response to UV light, was measured using photopic filters on the silicon detector. The response of the filtered detector approximated the luminosity curve. The $\Delta$ OD/Min was measured over the first five (5) seconds of UV exposure, then expressed on a per minute basis. The saturation optical density (OD) was taken under identical conditions as the $\Delta$ OD/Min, except UV exposure was continued for 20 minutes for the examples in Table 1 and for 15 minutes for the examples in Table 2. The lambda max reported in Tables 1 and 2 is the wavelength in the visible spectrum at which the maximum absorption of the activated (colored) form of the photochromic compound in poly (diethylene glycol his (allyl carbonate)) in Table 1 and in ethyl cellulose resin in Table 2 occurs. The Bleach Rate $T^{+b}$ ½ is the time interval in seconds for the absorbance of the activated form of the naphthopyran in the test polymers to reach one half the highest absorbance at room temperature (72° F., 22.2° C.) after removal of the source of activating light. Results are tabulated in Tables 1 and 2.

TABLE 1

| | Poly[diethylene glycol bis(allyl carbonate)] Samples | | | |
|---|---|---|---|---|
| | LAMBDA MAX | $\Delta$ OD/Min SENSITIVITY | $\Delta$ OD @ SATURATION | BLEACH RATE T ½ (SEC.) |
| COMPOUND EXAMPLE | | | | |
| 1 | 478 nm | 0.62 | 0.20 | 33 |
| 2 | 475 nm | 0.86 | 0.90 | 179 |
| 3 | 482 nm | 1.02 | 1.76 | >600 |
| 4 | 490 nm | 0.31 | 0.66 | 368 |
| 5 | 488 nm | 0.91 | 1.73 | 624 |
| 6 | 485 nm | 0.53 | 0.61 | 363 |
| 7 | 479 nm | 0.91 | 0.90 | 151 |
| 8 | 463 nm | 0.83 | 1.00 | 261 |
| COMPARATIVE EXAMPLE | | | | |
| 1 | 432 nm | 0.87 | 0.36 | 45 |
| 2 | 468 nm | 0.66 | 0.25 | 35 |
| 3 | 467 nm | 0.96 | 0.97 | 191 |
| a.* | 476 nm | 0.45 | 1.36 | >30 min. |

*a. Purchased 2,2-diphenyl-2H-naphtho[1,2-b]pyran

TABLE 2

| | Ethyl Cellulose Samples | | | |
|---|---|---|---|---|
| | LAMBDA MAX | Δ OD/Min SENSITIVITY | Δ OD @ SATURATION | BLEACH RATE T ½ (SEC.) |
| COMPOUND EXAMPLE | | | | |
| 9 | 459 nm | 0.66 | 0.31 | 41 |
| COMPARATIVE EXAMPLE | | | | |
| 1 | 432 nm | 0.87 | 0.31 | 32 |

The data tabulated in Tables 1 and 2 show that all of the Compound Examples, except Compound Examples 8 and 9, have lambda max values closer to 480 nm than Comparative Examples 1, 2, and 3. Compound Examples 8 and 9 have lambda max values much higher than Comparative Example 1 which has two phenyl groups at the 3 position of the pyran ring. Comparative Example "a" has a lamda max of 476 but the bleach rate is unacceptably slow for use in an ophthalmic lens application.

Although the present invention has been described with reference to the specific details of particular embodiments thereof, it is not intended that such details be regarded upon the scope of the invention except insofar as to the extent that they are included in the accompanying claims.

I claim:

1. A naphthopyran compound represented by the following graphic formula:

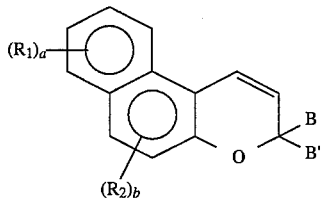

wherein, (a) $R_1$ and $R_2$ are each $C_1$-$C_{10}$ alkyl, $C_5$-$C_7$ cycloalkyl, halogen, R(R')N-, or the group, —O—L, wherein R and R' are each hydrogen or $C_1$-$C_3$ alkyl, L is $C_1$-$C_{12}$ alkyl, phenyl($C_1$-$C_3$)alkyl, $C_1$-$C_3$ alkylphenyl, $C_1$-$C_5$ alkylcarbonyl, halo($C_1$-$C_4$)alkylcarbonyl, $C_1$-$C_4$ monoalkylaminocarbonyl, acetonyl, pyridyl, substituted or unsubstituted arylcarbonyl, said aryl group being phenyl or naphthyl, said aryl substituents being $C_1$-$C_4$ alkyl, $C_1$-$C_4$ alkoxy, halogen, $C_5$-$C_7$ cycloalkyl, or $C_1$-$C_4$ alkyl substituted $C_5$-$C_7$ cycloalkyl, said halogen (or halo) groups being chloro, fluoro, or bromo; and a and b are each the integers 0, 1, or 2, provided that the sum of a and b is not more than 2;

(b) B is the substituted or unsubstituted aryl group, naphthyl or phenyl, said aryl substituents being $C_1$-$C_5$ alkyl, halo($C_1$-$C_5$)alkyl, hydroxy, $C_1$-$C_5$ alkoxy, $C_1$-$C_4$ alkoxy($C_1$-$C_4$)alkyl, halogen, or R(R')N-, wherein R and R' are each hydrogen or $C_1$-$C_3$ alkyl, and said halogen (or halo) groups being fluorine, chlorine, or bromine; and (c) B' is selected from the groups represented by the following graphic formulae:

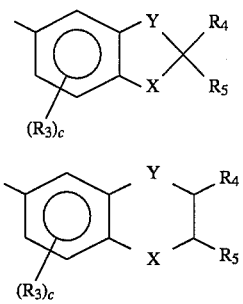

wherein X is nitrogen and Y is carbon; $R_4$ and $R_5$ are each hydrogen or $C_1$-$C_5$ alkyl; each $R_3$ is a $C_1$-$C_5$ alkyl, $C_1$-$C_5$ alkoxy, hydroxy, or halogen, said halogen being chloro, fluoro, or bromo, and c is an integer from 0 to 3.

2. A naphthopyran of claim 1 wherein:

(a) $R_1$ and $R_2$ are each $C_1$-$C_5$ alkyl, $C_5$-$C_6$ cycloalkyl, fluorine, bromine, R(R')N-, or the group —O—L, wherein R and R' are each hydrogen or $C_1$-$C_2$ alkyl, L is $C_1$-$C_4$ alkyl, $C_1$-$C_2$ alkylphenyl, phenyl($C_1$-$C_2$)alkyl, phenylcarbonyl, $C_1$-$C_2$ alkylcarbonyl, halo($C_1$-$C_2$)alkylcarbonyl, or $C_1$-$C_2$ monoalkylaminocarbonyl, said halo group being chloro or fluoro; and a and b are the integers 0 or 1; and (b) B is represented by the following graphic formula:

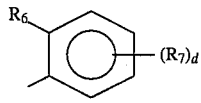

wherein $R_6$ is hydrogen, $C_1$-$C_4$ alkyl, $C_1$-$C_4$ alkoxy, fluoro, or chloro, each $R_7$ is a $C_1$-$C_4$ alkyl, $C_1$-$C_4$ alkoxy, hydroxy, chloro or fluoro, and d is an integer from 0 to 2.

3. A naphthopyran compound of claim 2 wherein $R_1$ and $R_2$ are each $C_1$-$C_3$ alkyl, fluorine or the group —O—L, wherein L is acetyl, benzoyl, methyl, or methylaminocarbonyl; B is phenyl or substituted phenyl, said phenyl substituents being fluoro, methyl, or methoxy; B' is indoline-5-yl, or 1,2,3,4-tetrahydroquinoline-6-yl and d is the integer 0 or 1.

4. A photochromic article comprising an organic host material and a photochromic amount of a naphthopyran compound represented by the following graphic formula:

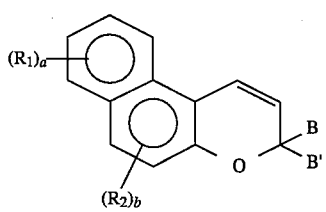

wherein,
  (a) $R_1$ and $R_2$ are each $C_1$-$C_{10}$ alkyl, $C_5$-$C_7$ cycloalkyl, halogen, R(R')N-, or the group, —O—L, wherein R and R' are each hydrogen or $C_1$-$C_3$ alkyl, L is $C_1$-$C_{12}$ alkyl, phenyl($C_1$-$C_3$)alkyl, $C_1$-$C_3$ alkylphenyl, $C_1$-$C_5$ alkylcarbonyl, halo($C_1$-$C_4$)alkylcarbonyl, $C_1$-$C_4$ monoalkylaminocarbonyl, acetonyl, pyridyl, substituted or unsubstituted arylcarbonyl, said aryl group being phenyl or naphthyl, said aryl substituents being $C_1$-$C_4$ alkyl, $C_1$-$C_4$ alkoxy, halogen, $C_5$-$C_7$ cycloalkyl, or $C_1$-$C_4$ alkyl substituted $C_5$-$C_7$ cycloalkyl, said halogen (or halo) groups being chloro, fluoro, or bromo; and a and b are each the integers 0, 1, or 2, provided that the sum of a and b is not more than 2;
  (b) B is the substituted or unsubstituted aryl group, naphthyl or phenyl, said aryl substituents being $C_1$-$C_5$ alkyl, halo($C_1$-$C_5$)alkyl, hydroxy, $C_1$-$C_5$ alkoxy, $C_1$-$C_4$ alkoxy($C_1$-$C_4$)alkyl, halogen, or R(R')N-, wherein R and R' are each hydrogen or $C_1$-$C_3$ alkyl, and said halogen (or halo) groups being fluorine, chlorine, or bromine; and
  (c) B' is selected from the groups represented by the following graphic formulae:

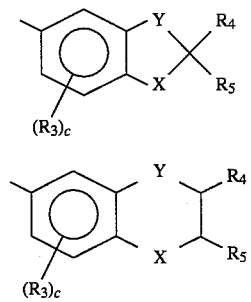

wherein X is nitrogen and Y is carbon; $R_4$ and $R_5$ are each hydrogen or $C_1$-$C_5$ alkyl; each $R_3$ is a $C_1$-$C_5$ alkyl, $C_1$-$C_5$ alkoxy, hydroxy, or halogen, said halogen being chloro, fluoro, or bromo, and c is an integer from 0 to 3.

5. The photochromic article of claim 4 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile, polyvinylbutyral and polymers of members of the group consisting of polyol(allyl carbonate) monomers, polyfunctional acrylate monomers, and diallylidene pentaerythritol monomers.

6. The photochromic article of claim 5 wherein:
  (a) $R_1$ and $R_2$ are each $C_1$-$C_5$ alkyl, $C_5$-$C_6$ cycloalkyl, fluorine, bromine, R(R')N-, or the group —O—L, wherein R and R' are each hydrogen or $C_1$-$C_2$ alkyl, L is $C_1$-$C_4$ alkyl, $C_1$-$C_2$ alkylphenyl, phenyl($C_1$-$C_2$)alkyl, $C_1$-$C_2$ alkylcarbonyl, halo($C_1$-$C_2$)alkylcarbonyl, or $C_1$-$C_2$ monoalkylaminocarbonyl, said halo group being chloro or fluoro; and a and b are the integers 0 or 1; and
  (b) B is represented by the following graphic formula:

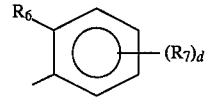

wherein $R_6$ is hydrogen, $C_1$-$C_4$ alkyl, $C_1$-$C_4$ alkoxy, fluoro, or chloro, each $R_7$ is a $C_1$-$C_4$ alkyl, $C_1$-$C_4$ alkoxy, hydroxy, chloro, or fluoro, and d is an integer from 0 to 2.

7. The photochromic article of claim 6 wherein $R_1$ and $R_2$ are each $C_1$-$C_3$ alkyl, fluorine or the group —O—L, wherein L is acetyl, benzoyl, methyl, or methylaminocarbonyl; B is phenyl or substituted phenyl, said phenyl substituents being fluoro, methyl, or methoxy; B' is indoline-5-yl, or 1,2,3,4-tetrahydroquinoline-6-yl and d is the integer 0 or 1.

8. The photochromic article of claim 7 wherein the organic host material is a solid transparent homopolymer or copolymer of diethylene glycol bis(allyl carbonate), carbonate-linked resin derived from 4,4'dioxydiphenol-2,2-propane and phosgene, poly(methylmethacrylate), polyvinylbutyral, or a polyurethane.

9. The photochromic article of claim 8 wherein the photochromic compound is present in an amount of from about 0.15 to 0.35 milligrams per square centimeter of organic host material surface to which the photochromic substance(s) is incorporated or applied.

10. The photochromic article of claim 9 wherein the article is a lens.

11. A photochromic article comprising a solid transparent polymerized organic host material and a photochromic amount of each of (a) a first photochromic substance selected from the group consisting of spiro(indoline) naphthoxazines, spiro(indoline) pyridobenzoxazines, and spiro(indoline) benzoxazines, and benzopyrans or naphthopyrans having a nitrogen-containing substituent in the 2-position of the pyran ring, and (b) a second photochromic substance selected from naphthopyran compounds represented by the following graphic formula:

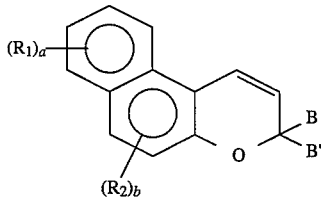

wherein,
  (a) $R_1$ and $R_2$ are each $C_1$-$C_{10}$ alkyl, $C_5$-$C_7$ cycloalkyl, halogen, R(R')N-, or the group, —O—L, wherein R and R' are each hydrogen or $C_1$-$C_3$ alkyl, L is $C_1$-$C_{12}$ alkyl, phenyl($C_1$-$C_3$)alkyl, $C_1$-$C_3$ alkylphenyl, $C_1$-$C_5$ monoalkylcarbonyl, halo($C_1$-$C_4$)alkylcarbonyl, $C_1$-$C_4$ alkylaminocarbonyl, acetonyl, pyridyl, substituted or unsubstituted arylcarbonyl, said aryl group being phenyl or naphthyl, said aryl substituents being $C_1$-$C_4$ alkyl, $C_1$-$C_4$ alkoxy, halogen, $C_5$-$C_7$ cycloalkyl, or $C_1$-$C_4$ alkyl substituted $C_5$-$C_7$ cycloalkyl, said halogen (or halo) groups being chloro, fluoro, or bromo; and a and b are each the integers 0, 1, or 2, provided that the sum of a and b is not more than 2;

(b) B is the substituted or unsubstituted aryl group, naphthyl or phenyl, said aryl substituents being $C_1$-$C_5$ alkyl, halo($C_1$-$C_5$)alkyl, hydroxy, $C_1$-$C_5$ alkoxy, $C_1$-$C_4$ alkoxy($C_1$-$C_4$)alkyl, halogen, or R(R')N-, wherein R and R' are each hydrogen or $C_1$-$C_3$ alkyl, and said halogen (or halo) groups being fluorine, chlorine, or bromine; and (c) B' is selected from the groups represented by the following graphic formulae:

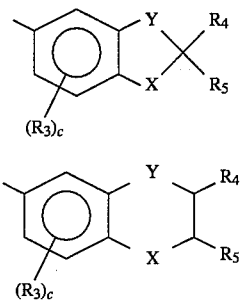

wherein X is nitrogen and Y is carbon; $R_4$ and $R_5$ are each hydrogen or $C_1$-$C_5$ alkyl; each $R_3$ is a $C_1$-$C_5$ alkyl, $C_1$-$C_5$ alkoxy, hydroxy or halogen, said halogen being chloro, fluoro, or bromo, and c is an integer from 0 to 3.

12. The photochromic article of claim 11 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethane, poly(ethylene terephthalate), polystyrene, copoly(styrene-methylmethacrylate), copoly(styrene-acrylonitrile, polyvinylbutyral and polymers of members of the group consisting of polyol(allyl carbonate) monomers, polyfunctional acrylate monomers, and diallylidene pentaerythritol monomers.

13. The photochromic article of claim 12 wherein:

(a) $R_1$ and $R_2$ are each $C_1$-$C_5$ alkyl, $C_5$-$C_6$ cycloalkyl, fluorine, bromine, R(R')N-, or the group —O—L, wherein R and R' are each hydrogen or $C_1$-$C_2$ alkyl, L is $C_1$-$C_4$ alkyl, $C_1$-$C_2$ alkylphenyl, phenyl($C_1$-$C_2$)alkyl, phenylcarbonyl, $C_1$-$C_2$ alkylcarbonyl, halo($C_1$-$C_2$)alkylcarbonyl, or $C_1$-$C_2$ monoalkylaminocarbonyl, said halo group being chloro or fluoro; and a and b are the integers 0 or 1; and (b) B is represented by the following graphic formula:

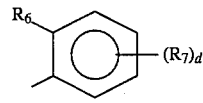

wherein $R_6$ is hydrogen, $C_1$-$C_4$ alkyl, $C_1$-$C_4$ alkoxy, fluoro, or chloro, each $R_7$ is a $C_1$-$C_4$ alkyl, $C_1$-$C_4$ alkoxy, hydroxy, chloro, or fluoro, and d is an integer from 0 to 2.

14. The photochromic article of claim 13 wherein $R_1$ and $R_2$ are each $C_1$-$C_3$ alkyl, fluorine or the group —O—L, wherein L is acetyl, benzoyl, methyl, or methylaminocarbonyl; B is phenyl or substituted phenyl, said phenyl substituents being fluoro, methyl, or methoxy; B' is indoline-5-yl, or 1,2,3,4-tetrahydroquinoline-6-yl and d is the integer 0 or 1.

15. The photochromic article of claim 14 wherein the organic host material is a solid transparent homopolymer or copolymer of diethylene glycol bis(allyl carbonate), carbonate-linked resin derived from 4,4'dioxydiphenol-2,2-propane and phosgene, poly(methylmethacrylate), polyvinylbutyral, or a polyurethane.

16. The photochromic article of claim 15 wherein the photochromic compound is present in an amount of from about 0.15 to 0.35 milligrams per square centimeter of organic host material surface to which the photochromic substance(s) is incorporated or applied.

17. The photochromic article of claim 16 wherein the weight ratios of the first photochromic substance to the naphthopyran compound is from about 1:3 to about 3:1.

18. The photochromic article of claim 17 wherein the article is an ophthalmic lens.

* * * * *